(12) United States Patent
Miyake et al.

(10) Patent No.: US 6,659,165 B1
(45) Date of Patent: Dec. 9, 2003

(54) METAL CASTING DEVICE AND METAL CASTING METHOD USING THE SAME

(75) Inventors: Matsuyuki Miyake, Kyoto (JP); Yasuhiko Kuwamura, Kyoto (JP)

(73) Assignee: Nissin Dental Products, Inc., Kyoto (JP)

( * ) Notice: Subject to any disclaimer, the term of this patent is extended or adjusted under 35 U.S.C. 154(b) by 0 days.

(21) Appl. No.: 10/169,463

(22) PCT Filed: Jan. 7, 2000

(86) PCT No.: PCT/JP00/00033

§ 371 (c)(1), (2), (4) Date: Jul. 2, 2002

(87) PCT Pub. No.: WO01/49434

PCT Pub. Date: Jul. 12, 2001

(51) Int. Cl.$^7$ .............................................. B22D 27/02
(52) U.S. Cl. ...................... 164/495; 164/136; 164/337
(58) Field of Search ................. 164/133, 134, 164/135, 136, 335, 336, 337, 495

(56) References Cited

U.S. PATENT DOCUMENTS 2,136,840 A  * 11/1938 Buckler ....................... 164/136
3,807,484 A  * 4/1974 von Starck ................... 164/500
6,386,265 B1 * 5/2002 Usui ............................ 164/114

* cited by examiner

Primary Examiner—M. Alexandra Elve
Assistant Examiner—Len Tran
(74) Attorney, Agent, or Firm—Kirschstein, etal.

(57) ABSTRACT

In an apparatus for casting a metal comprise a crucible (2), a casting mold (3) and an electrode rod (10) for an arc discharge are provided in an interior portion of a casting chamber (1) capable of controlling a pressure, a supporting shaft (6) exists in a side of an outflow end portion of the crucible (2) close to a charging port (5) of the casting mold (3), the crucible (2) can be tilted around the supporting shaft (6), a crucible tilting means (7) exists in a side of a non-outflow end portion of the crucible (2), a clearance between a metal and the electrode rod is kept substantially constant after the arc melting of the metal (4) on the crucible (2) is started and the melting of the metal (4) makes progress and until the metal (4) in the melting state drops down due to the tilting of the crucible (2), and the arc discharge is kept during a period that the metal (4) flows and drops down. At this time, it is preferable to connect a pressure reduction pump (12) and a pressurized gas supply source (13) to the casting chamber (1), make a gas supply pressure $P_1$ having a controlled pressure larger than a gas pressure $P_2$ required for casting, and shut off the supply of the pressurized gas at a time of getting to the gas pressure $P_2$.

4 Claims, 5 Drawing Sheets

(a) CASE OF USING THE APPARATUS OF THE PRESENT INVENTION (b) CASE OF USING THE APPARATUS OF THE PRIOR ART (a) CASE OF USING THE APPARATUS OF THE PRESENT INVENTION (b) CASE OF USING THE APPARATUS OF THE PRIOR ART

Fig. 5

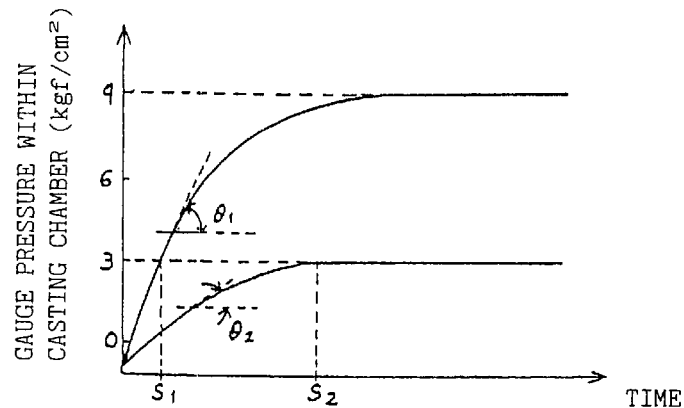

$S_1$ : TIME REQUIRED UNTIL GAUGE PRESSURE WITHIN CASTING CHAMBER GETS TO 3 kgf/cm², IN CASE THAT SUPPLY GAS PRESSURE IS 10 kgf/cm²
$S_2$ : TIME REQUIRED UNTIL GAUGE PRESSURE WITHIN CASTING CHAMBER GETS TO 3 kgf/cm², IN CASE THAT SUPPLY GAS PRESSURE IS 4 kgf/cm²
$\theta_1$ : HIGH PRESSURE INCREASE RATE
$\theta_2$ : LOW PRESSURE INCREASE RATE

Fig. 6

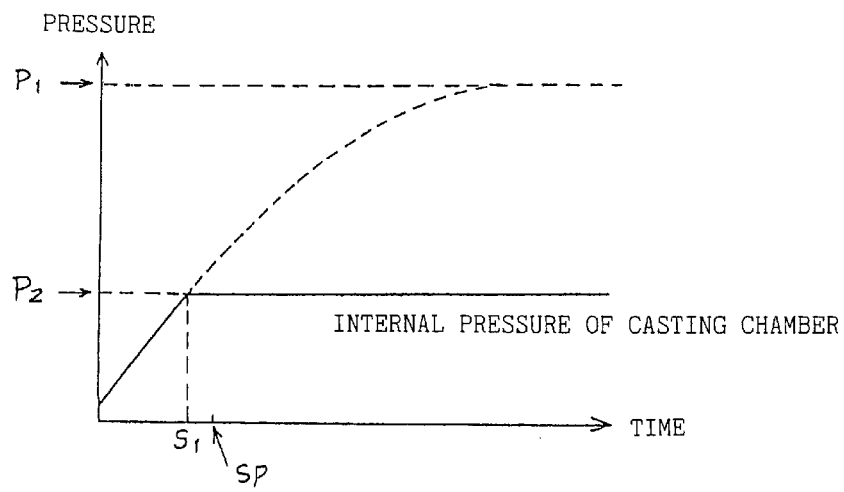

$P_1$ : SET PRESSURE IN PRESSURE ADJUSTING DEVICE
$P_2$ : PRESSURE VALUE REQUIRED FOR CASTING
$S_1$ : TIME REQUIRED UNTIL INTERNAL PRESSURE GETS TO $P_2$, AT A TIME WHEN SUPPLY GAS PRESSURE IS $P_1$
$S_p$ : TIME CAPABLE OF FLOWING OF MOLTEN METAL

METAL CASTING DEVICE AND METAL CASTING METHOD USING THE SAME

TECHNICAL FIELD

The present invention relates to an apparatus for casting a metal which is suitable for casting a metal used in a field of dentistry, for example, a metal having a high melting point such as a titanium or the like. Further, the present invention relates to a method capable of executing a casting with a higher casting capacity by using the apparatus mentioned above.

BACKGROUND ART

Up to the present, a prosthetic appliance has been used at a time of repairing a decayed tooth or a dropout tooth, and the metal having a high melting point, for example, the titanium, a zirconium, a platinum or the like and an alloy thereof is used as a material constituting the prosthetic appliance for the dentistry. Among them, the titanium is particularly a very suitable material in view of a strength, a lightness, a corrosion resistance, a biocompatibility, a cost and the like, and is widely used.

Further, at a time of forming the prosthetic appliance for the dentistry by using the metal mentioned above, a casting mold in which a cavity portion having a desired shape is formed is used, and it is general to directly inject the metal mentioned above in a melting state into the cavity portion of the casing mold so as to mold, and thereafter break the casing mold so as to take out a cast product.

As a general apparatus for casting the metal which has been used, there is a structure in which a tiltable metal crucible 2 is arranged above a casting mold 3 in which a casting cavity 9 is formed, as shown in FIG. 2. The apparatus is structured such that a metal 4 mounted on an upper surface of the crucible 2 is arc-melted in an ambient atmosphere of inert gas (for example, an argon gas), the crucible 2 is tilted at a time when the metal 4 is completely melted, thereby pouring the molten metal into a casting port 5 of the casing mold 3, an opening and closing valve (an electric opening and closing valve) 14 is opened, whereby a pressurized gas flows into an interior portion of a casting chamber 1 from a pressurized gas supply source 13 at a pressure value set by a pressure adjusting device 17, and the interior portion of the casting chamber 1 is gas-pressurized, thereby executing a casting. In this apparatus, the crucible 2 moves so as to tilt to a lower side around a supporting shaft 6 (a supporting point), and stops at a position indicated by reference numeral 2'. In this case, the casting capacity of the apparatus for casting the metal is improved in proportion to the pressure value. In this case, as an electrode rod 10 in a cathode side of the apparatus shown in FIG. 2, a general tungsten electrode rod is used.

However, in the apparatus for casting the metal shown in FIG. 2, since the supporting shaft 6 in the crucible 2 arranged above the casting mold 3 is positioned in a far side from the casting port 5 of the casing mold 3, it is necessary to provide a clearance for preventing the crucible 2 after being tilted from being in contact with the casing mold 3, between the crucible 2 and the casting mold 3, so that the molten metal drops down along a distance larger than the clearance. Since the clearance is generally about 4 to 5 cm, the apparatus mentioned above has a problem that it is hard to drop down the metal in the melding state into the casting cavity 9 within the casting mold 3 with keeping a high temperature, and there is a limit to make the apparatus compact. Further, in the case of the apparatus having the structure mentioned above, since the molten metal drops down at a fixed width, there are problems that the molten metal attaches to a periphery of the casting port 5 and a dispersion is generated in view of the dropping position of the metal.

Further, in the case of this apparatus, since a distance between the metal and the electrode rod is changed (enlarged) when the crucible starts tilting, there is a problem that an arc discharge is immediately stopped and a proper overheat of the molten metal is not absolutely achieved, whereby it is hard to cast the molten metal having the high temperature into the casting mold 3.

Further, aside from this, in the case of the apparatus having the structure shown in FIG. 2, since a pressure value pertinent to the casting capacity is univocally determined by the pressure adjusting device 17, it is necessary to set a set pressure value of the pressure adjusting device 17 to a higher value in the case of intending to obtain a higher casting capacity, and accordingly, there is a problem that it is necessary to reinforce a pressure resisting structure of the casting chamber 1 more. Further, since the gas is supplied to the interior portion of the casting chamber 1 until getting to the pressure value set by the pressure adjusting device 17, there is a problem that a greater amount of gas is consumed in one casting step.

DISCLOSURE OF THE INVENTION

An object of the present invention is to provide an apparatus for a metal casting which can solve the problems mentioned above, and has a structure capable of casting a high temperature metal, in particular a metal having a high melting point for dentistry such as a titanium or the like, in a melting state due to an arc discharge without reducing a temperature.

Further, an another object of the present invention is to provide an apparatus for casting a metal which can use a casting chamber having a simple pressure resisting structure while obtaining a higher casting capacity by utilizing a pressurized gas, and can reduce an amount of consumption of the pressurized gas in the casting step.

Further, the other object of the present invention is to provide a method capable of executing a casting process with a higher casting capacity by using the apparatus mentioned above.

In order to achieve the structure suitable for casting the metal having the high melting point, in accordance with the present invention, there is provided an apparatus for casting a metal comprising:

a crucible 2 and a casting mold 3 provided in an interior portion of a casting chamber 1 capable of controlling an internal pressure;

an electrode rod 10 for melting a metal 4 mounted on the crucible 2 in accordance with an arc discharge, the electrode rod 10 being provided above the crucible 2;

the crucible 2 being tiltable around a supporting shaft 6 in such a manner as to pour the metal 4 melted on the crucible 2 into a casting port 5 of the casting mold 3;

the supporting shaft 6 being positioned in a side of an outflow end portion of the crucible 2 close to the charging port 5; and a tilting means 7 for drawing up a non-outflow end portion to an upper side so as to tilt the crucible, the tilting means 7 being provided in a side of the non-outflow end portion of the crucible 2, wherein the supporting shaft 6 is provided at a position at which a clearance between the metal 4 and a front end of the electrode rod 10 is kept substantially constant after the melting of the metal 4 in accordance with the arc discharge on the crucible 2 is started and the melting of the metal 4 makes progress and until the metal 4 in the melting state fluidizes and drops down due to the tilting of the crucible 2, and the arc discharge is controlled so that the arc discharge is carried over between the metal 4 in the melting state and the front end of the electrode rod 10 during a period that the crucible 2 is tilted and the metal 4 in the melting state fluidizes and drops down on the crucible 2.

Further, in accordance with the present invention, there is provided an apparatus for casting a metal having the structure mentioned above, wherein a pressure reduction pump 12 capable of making the interior portion of the casting chamber 1 in a pressure reduced state, and a pressurized gas supply source 13 supplying a pressurized gas to the interior portion of the casting chamber 1 are connected to the casting chamber 1, an inflow of the pressurized gas supplied from the pressurized gas supply source 13 into the casting chamber 1 is controlled by an opening and closing valve 14, the opening and closing valve 14 becomes in an open state at a time when a gas supply pressure $P_1$ of the pressurized gas supply source 13 is larger than a gas pressure $P_2$ required for casting the metal in the melting state into a casting mold cavity 9 of the casting mold 3 with no lack of casting and the metal 4 melted on the crucible 2 is poured into the casting port 5 of the casting mold 3 in accordance with the tilting of the crucible 2, and the inflow of the pressurized gas into the casting chamber 1 is shut off by the opening and closing valve 14 at a timing when the pressurized gas flows into the casting chamber 1 from the pressurized gas supply source 13 and an internal pressure of the casting chamber 1 gets to the gas pressure $P_2$.

Further, in accordance with the present invention, there is provided a metal casting method of casting a metal by using an apparatus for casting a metal having a structure in which a crucible 2 and a casting mold 3 are provided in an interior portion of a casting chamber 1 capable of controlling an internal pressure, an electrode rod 10 for melting a metal 4 mounted on the crucible 2 in accordance with an arc discharge is provided above the crucible 2, the crucible 2 is tiltable around a supporting shaft 6 in such a manner as to pour the metal 4 melted on the crucible 2 into a casting port 5 of the casting mold 3, the supporting shaft 6 is positioned in a side of an outflow end portion of the crucible 2 close to the casting port 5, and is provided at a position at which a clearance between the metal 4 and a front end of the electrode rod 10 is kept substantially constant after the melting of the metal 4 in accordance with the arc discharge on the crucible 2 is started and the melting of the metal 4 makes progress and until the metal 4 in the melting state fluidizes and drops down due to the tilting of the crucible 2, and a tilting means 7 for drawing up a non-outflow end portion to an upper side so as to tilt the crucible is provided in a side of the non-outflow end portion of the crucible 2, wherein an electric voltage is applied between the metal 4 and the electrode rod 10 so as to generate an arc discharge after mounting the metal 4 on the crucible 2, the crucible 2 is tilted at a timing that the metal 4 is melted so as to become in a state of capable of fluidizing, and the arc discharge is kept between the metal 4 in the melting state and the front end of the electrode rod 10 even during a period that the metal 4 in the melting state fluidizes on the crucible 2 so as to drop down at a time of pouring the metal 4 in the melting state into the casting port 5 of the casting mold 3.

Further, in accordance with the present invention, there is provided a method as recited in the above, wherein an apparatus having a structure in which a pressure reduction pump 12 capable of making the interior portion of the casting chamber 1 in a pressure reduced state, and a pressurized gas supply source 13 supplying a pressurized gas to the interior portion of the casting chamber 1 are connected to the casting chamber 1, and an inflow of the pressurized gas supplied from the pressurized gas supply source 13 into the casting chamber 1 is controlled by an opening and closing valve 14 is used as the apparatus for casting the metal, and in which a gas supply pressure $P_1$ of the pressurized gas supply source 13 is made larger than a gas pressure $P_2$ required for casting the metal in the melting state into a casting mold cavity 9 of the casting mold 3 with no lack of casting, the opening and closing valve 14 is controlled so as to be in an open state at a time when the metal 4 melted on the crucible 2 due to the tilting of the crucible 2 is poured into the casting port 5 of the casting mold 3, and so that the pressurized gas flows into the casting chamber 1 from the pressurized gas supply source 13, and the inflow of the pressurized gas into the casting chamber 1 is shut off by the opening and closing valve 14 at a timing when an internal pressure of the casting chamber 1 gets to the gas pressure $P_2$.

BRIEF DESCRIPTION OF THE DRAWINGS

FIG. 5 is a view showing one example of an internal pressure-time curve of a casting chamber at a time of charging the gas into the casting chamber of the apparatus for casting the dental metal having a general internal volume at a pressure of 4 kgf/cm$^2$ and 10 kgf/cm$^2$.

FIG. 6 is a view showing a relation between a gas supply pressure $P_1$ of a pressurized gas supply source 13 and a gas pressure $P_2$ required for casting a metal in a melting state within a casting cavity 9 of a casting mold 3 with no lack of casting, in the apparatus for casting the metal in accordance with the present invention.

BEST MODE FOR CARRYING OUT THE INVENTION

Figure 1:
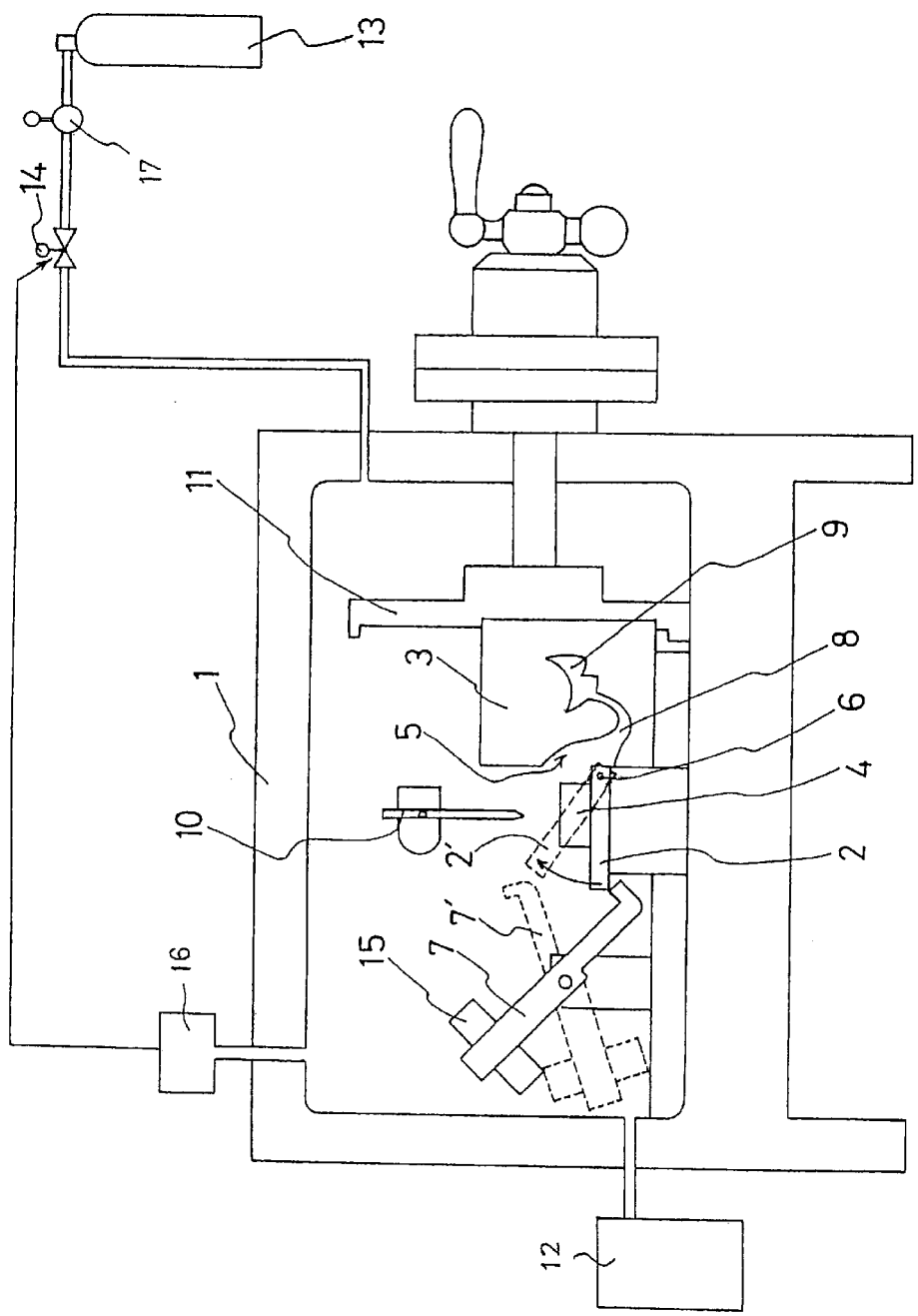
FIG. 1 is a view showing a state at a time of executing a casting by using an apparatus for casting a metal in accordance with the present invention.
Figure 2:
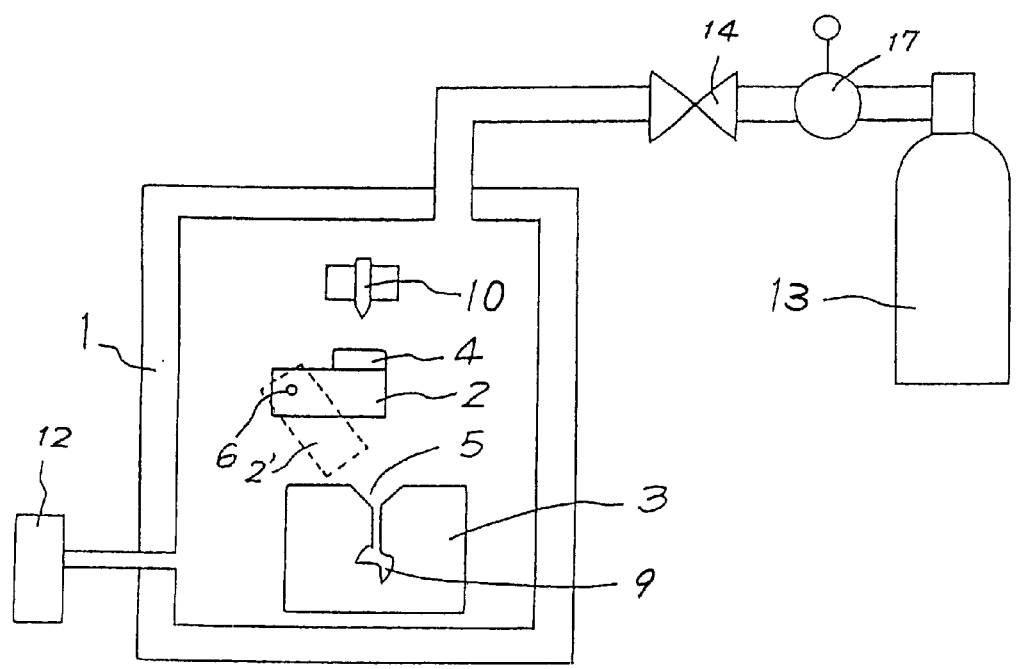
FIG. 2 is a view showing an internal structure of a general apparatus for casting a metal which has been conventionally known.

A description will be given below of an embodiment of an apparatus for casting a metal in accordance with the present invention with reference to the accompanying drawings, however, the present invention is not limited to this. FIG. 1 is a view showing a state at a time of executing a casting operation by using the apparatus for casting the metal in accordance with the present invention.

In the apparatus for casting the metal in accordance with the present invention, a crucible 2 and a casting mold 3 are provided in an interior portion of a casting chamber 1 having a structure which can control an internal pressure, and an electrode rod 10 for arc-melting a metal 4 mounted on the crucible 2 is provided above the crucible 2. A general tungsten electrode rod or the like is used for the electrode rod 10, and a metal crucible is used as the crucible 2. Further, the crucible 2 has a structure which can tilt around a supporting shaft 6 in such a manner as to pour the metal 4 arc melted on an upper surface thereof into a casting port 5 of the casting mold 3.

The supporting shaft 6 in the apparatus in accordance with the present invention is positioned in a side of an outflow end portion of the crucible 2 close to the casting port 5, and the structure is made such that non-outflow end portion side (that is, a side apart from the casting port 5) of the crucible 2 is lifted up around the supporting shaft 6. Further, the supporting shaft 6 is provided at a position at which a clearance between the metal 4 and a front end of the electrode rod 10 is kept substantially constant after the melting of the metal 4 in accordance with the arc discharge on the crucible 2 is started and the melting of the metal 4 makes progress and until the metal 4 in the melting state fluidizes and drops down due to the tilting of the crucible 2, and an electric current continuously flows between both of the elements even after the crucible 2 starts tilting, whereby an arc discharge can be continuously achieved. Accordingly, an electric voltage is applied between the metal 4 and the electrode rod 10 during a period that the crucible 2 is tilted and the metal 4 in the melting state fluidizes and drops down, whereby a control is executed so that the arc discharge between the metal 4 and the electrode rod 10 is kept.

Figure 3:
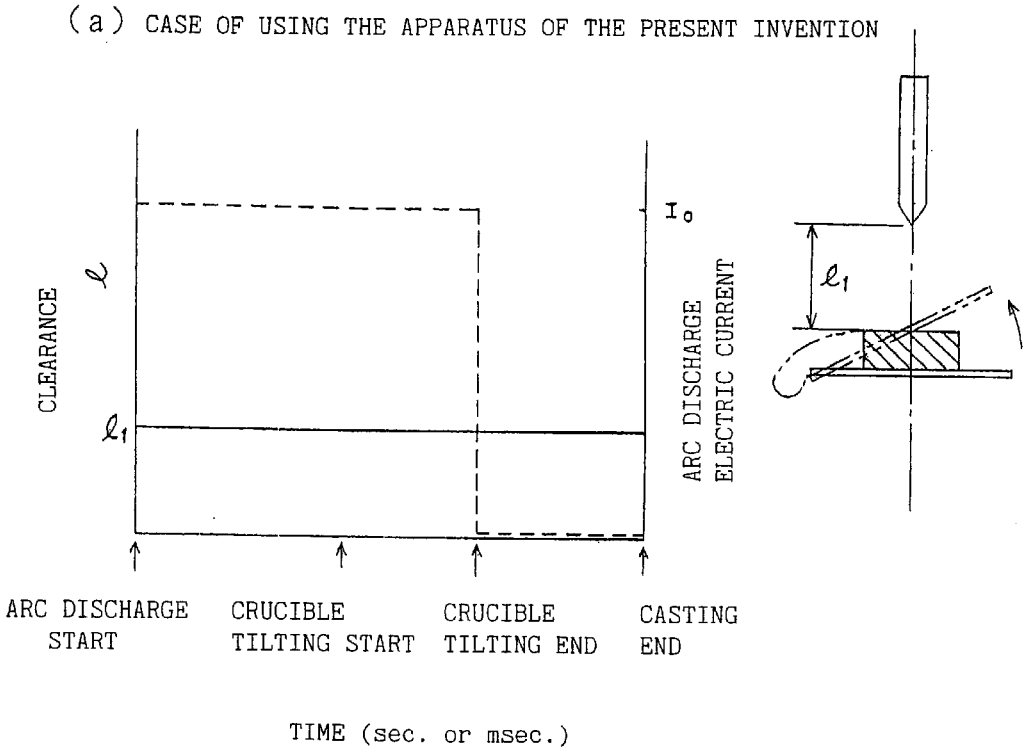
FIG. 3(a) is a graph (left view) showing a fluctuation with time of a clearance between a metal and an electrode rod and a fluctuation with time of an arc discharge current from an arc discharge start till a casting end, and a view (right view) showing a state in which the clearance between the metal and the electrode rod changes due to a tilting of a crucible, in the case of using the apparatus in accordance with the present invention.
FIG. 3(b) is a graph (left view) showing a fluctuation with time of a clearance between a metal and an electrode rod and a fluctuation with time of an arc discharge current from an arc discharge start till a casting end, and a view (right view) showing a state in which the clearance between the metal and the electrode rod changes due to a tilting of a crucible, in the case of using the apparatus in accordance with the prior art.
Figure 3:
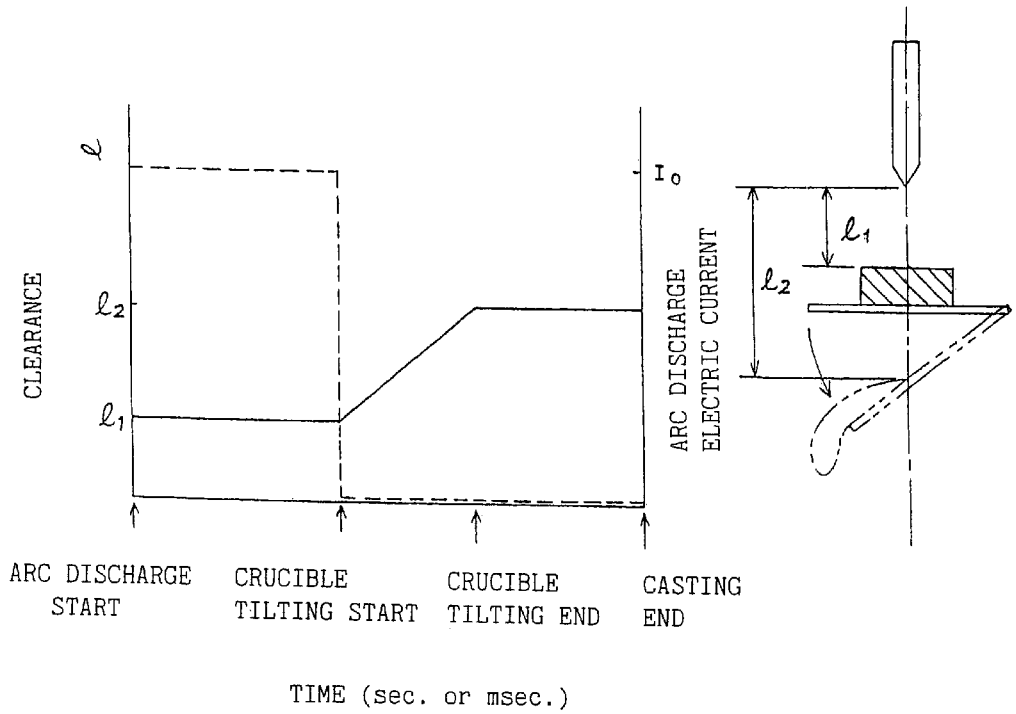

FIG. 3(a) is a graph (left view) showing a fluctuation with time of a clearance (1) between a metal and an electrode rod and a fluctuation with time of an arc discharge current from an arc discharge start till a casting end, and a view (right view) showing a state in which the clearance between the metal and the electrode rod changes due to a tilting of a crucible, in the case of using the apparatus in accordance with the present invention, and FIG. 3(b) is a graph (left view) showing a fluctuation with time of a clearance (1) between a metal and an electrode rod and a fluctuation with time of an arc discharge current from an arc discharge start till a casting end, and a view (right view) showing a state in which the clearance between the metal and the electrode rod changes due to a tilting of a crucible, in the case of using the apparatus in accordance with the prior art.

As shown in FIG. 3(a), in the case of the apparatus in accordance with the present invention, a clearance ($1_1$) between the metal and the electrode rod is constant without fluctuating (shown by a solid line) even when the crucible is tilted after the arc discharge start till the casting end, so that the arc discharge can be kept even when the crucible starts tilting, the arc discharge can be achieved until the tilting operation of the crucible is finished (until the metal vanishes away on the crucible), it is possible to optionally select the stop timing of the arc discharge, and it is possible to prevent the temperature of the metal in the melting state from being reduced. In this view, a dotted line shows a fluctuation with time of the arc discharge electric current.

On the contrary, in the case of the conventional apparatus, as shown in FIG. 3(b), since the clearance between the metal and the electrode rod changes from $1_1$ to $1_2$ between before and after the crucible tilts, the arc discharge is necessarily stopped when the crucible starts tilting, and it is impossible to prevent the temperature of the metal from being reduced after the arc discharge is stopped until the metal is poured into the casting mold.

In this case, in the apparatus in accordance with the present invention, a tilting means 7 for drawing up the non-outflow end portion to an upper side so as to tilt the crucible is provided in a side of the non-outflow end portion of the crucible 2, and a structure of the tilting means 7 is not limited to the structure exemplified in the drawing. As the tilting means 7, a tilting means having the same structure as a seesaw as shown in FIG. 1 is particularly preferable. The tilting means 7 shown in FIG. 1 is structured such that one end portion (an end portion close to the crucible 2) is in contact with a bottom surface in the side of the non-outflow end portion of the crucible 2, and a weight 15 is mounted to other end portion in such a manner as to draw up the crucible 2 around the supporting shaft 6. In the case of the apparatus shown in FIG. 1, in a state before the metal 4 is melted, the tilting means 7 is kept in a state in which the side of the crucible 2 descends as shown by a solid line, and the crucible 2 is positioned horizontally, however, at a time when the metal 4 is completely melted, the hold of the tilting means 7 is cancelled, the end portion of the tilting means 7 in the side to which the weight 15 is mounted descends, the crucible 2 simultaneously tilts around the supporting shaft 6, and the crucible and the tilting means respectively get to positions 2' and 7' shown by dotted lines.

In accordance with the present invention, the structure of the casting mold 3 is not particularly limited, the structure may be made as shown in FIG. 1 such that the casting port 5 is provided in the side wall side, the crucible 2 is arranged so as to be close to the casting port 5, and a casting cavity 9 is formed in an interior portion of the casting mold 3 so as to be obliquely upward via a storage portion 8 formed from the casting port 5 toward an obliquely lower side, or the structure may employ a general structure in which the casing port 5 is provided in a side of the upper surface of the casing mold 3. In the former case, the metal casting is executed in accordance with a method utilizing the gas pressure mentioned below. In this case, in the apparatus shown in FIG. 1, a slidably fixing member 11 is provided so as to correspond to the casting mold 3 having various kinds of sizes.

In the apparatus for casting the metal in accordance with the present invention shown in FIG. 1, a pressure reduction pump 12 capable of making the interior portion of the casting chamber 1 in a pressure reduced state, and a pressurized gas supply source 13 (in general, an inert gas bomb such as an argon gas bomb or the like) supplying a pressurized gas to the interior portion of the casting chamber 1 are connected to the casting chamber 1 having an air tightness, whereby an inflow of the pressurized gas supplied from the pressurized gas supply source 13 into the casting chamber 1 is controlled by an opening and closing valve 14. Further, in the case of this apparatus, before casting, the opening and closing valve 14 is closed, and the interior portion of the casting chamber 1 is made in the pressure reduced state by the pressure reduction pump 12, and at a time of casting the molten metal in accordance with the arc discharge into the casting mold cavity 9 of the casting mold 3, the pressure reduction by the pressure reduction pump 12 is shut off, whereby the opening and closing valve 14 becomes in an open state, the interior portion of the casting chamber 1 is pressurized to a predetermined pressure, and the casting operation is executed. In this case, a pressure detecting device 16 capable of detecting the internal pressure of the casting chamber 1, and a pressure adjusting device 17 for previously adjusting the pressure of the gas supplied from the pressurized gas supply source 13 to a fixed pressure, that is, a pressure required for casting the molten metal to the casting cavity 9 within a time at which the molten metal can fluidize are provided in the casting chamber 1 in the apparatus in accordance with the present invention of the pressure control type exemplified in FIG. 1. In the present invention, it is general that an electric type pressure detecting device is used as the pressure detecting device 16, however, the structure is not limited to this.

In the case of using the apparatus for casting the metal shown in FIG. 1, it is preferable that at a timing that a gas supply pressure $P_1$ of the pressurized gas supply source 13 is larger than a gas pressure $P_2$ required for casting the metal in the melting state into the casting mold cavity 9 of the casting mold 3 with no lack of casting, the opening and closing valve 14 becomes in an open state at a time when the metal 4 melted on the crucible 2 due to the tilting of the crucible 2 is poured into the casting port 5 of the casting mold 3, the pressurized gas flows into the casting chamber 1 from the pressurized gas supply source 13, and the internal pressure of the casting chamber 1 gets to the gas pressure $P_2$, a control signal is sent to the opening and closing valve 14 from the pressure detecting device 16, and the inflow of the pressurized gas into the casting chamber 1 is shut off in a moment of time by the opening and closing valve 14. A casting product obtained by using the apparatus in accordance with the present invention having the structure in which the interior portion of the casting chamber is quickly pressurized is uniform, is excellent in view of a casting property (a faithfulness of pattern), and can obtain a minimum inert gas consumption amount required for casting the metal in the melting state into the casting cavity 9 with no lack of casting. Since the matter that the inert gas consumption amount is a little means in other words a matter that the internal pressure of the casting chamber 1 is reduced, the pressure resisting structure requires a strength necessary and minimum for the target casting.

In accordance with the present invention, the internal pressure of the casting chamber 1 is adjusted so as not to be over the gas pressure $P_2$ by the opening and closing valve 14, and the opening and closing valve 14 may be structured such that the opening and closing operation of the valve is electrically controlled (an electric type opening and closing valve), or mechanically controlled (a mechanical type opening and closing valve). Further, the opening and closing valve 14 may be controlled to be opened or closed on the basis of the signal output from the pressure detecting device 16, or may be of a time control type which is controlled to be opened during a period that the internal pressure of the casting chamber 1 gets to the gas pressure $P_2$.

Figure 4:
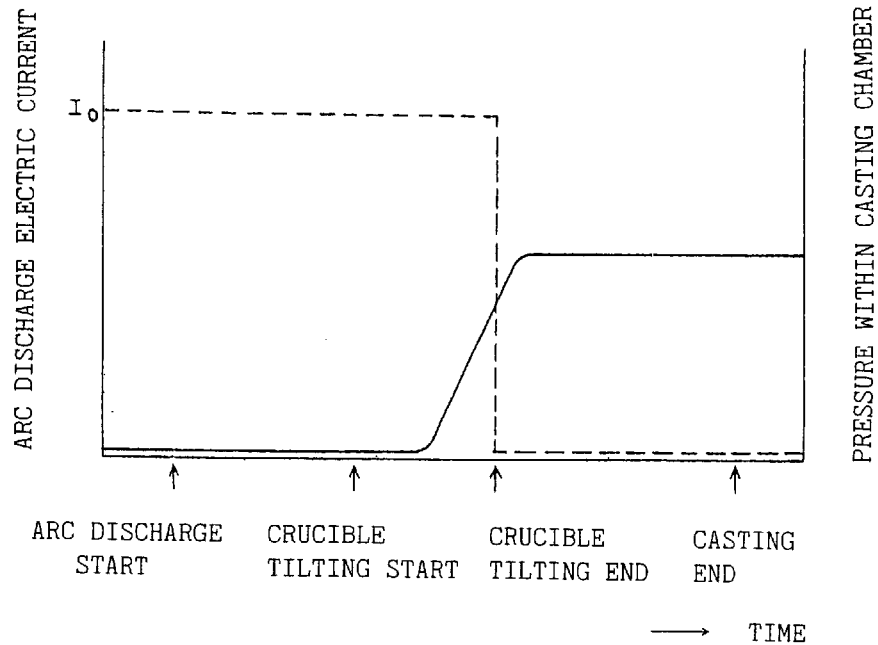
FIG. 4(a) is a graph showing a fluctuation with time of an arc discharge current and a fluctuation with time of a pressure within a casting chamber from an arc discharge start till a casting end, in the case of using the apparatus in accordance with the present invention.
FIG. 4(b) is a graph showing a fluctuation with time of an arc discharge current and a fluctuation with time of a pressure within a casting chamber from an arc discharge start till a casting end, in the case of using the apparatus in accordance with the prior art.
Figure 4:
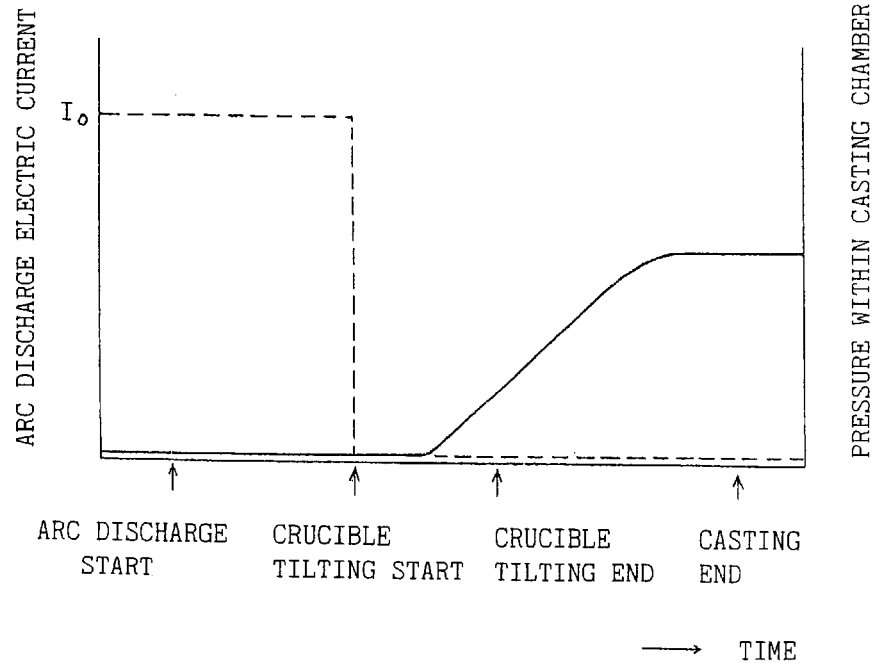

FIG. 4(a) is a graph showing a fluctuation with time of an arc discharge current, and a fluctuation with time of a pressure within a casting chamber from an arc discharge start till a casting end, in the case of using the apparatus in accordance with the present invention, and FIG. 4(b) is a graph showing a fluctuation with time of an arc discharge current and a fluctuation with time of a pressure within the casting chamber from an arc discharge start till a casting end, in the case of using the apparatus in accordance with the prior art.

As shown in FIG. 4(a), in the case of the apparatus in accordance with the present invention, it is known that the arc discharge electric current is kept to a fixed value even when the crucible starts tilting, a heat application to the metal on the crucible is kept (shown by a dotted line), and the interior portion of the casting chamber is pressurized to a predetermined pressure value for a short time after the metal in the melting state is poured into the casting mold. On the contrary, in the case of the conventional apparatus, as shown in FIG. 4(b), the arc discharge is stopped substantially at the same time when the crucible starts tilting, the metal in the melting state is not heated at all during the period of being poured into the casting mold, and the time required for getting to the predetermined pressure value becomes longer than the case (a), so that it is hard to obtain a sufficient casting property in the case of casting the metal having a high melting point.

FIG. 5 is one example of an internal pressure-time curve of the casting chamber at a time of charging the gas into the casting chamber of the apparatus for casting the dental metal having a general internal volume at a pressure of 4 kgf/cm$^2$ and 10 kgf/cm$^2$. The gas charge corresponds to a gas stream from a high pressure side to a low pressure side, and the larger the pressure difference is, the earlier and stronger the molten metal flows into the casting mold cavity. As shown in FIG. 5, in the case of charging the gas into the casting chamber, at a timing that the pressure difference is reduced together with the inflow of gas and the pressure difference is finally lost, the movement of gas is lost and the charging operation is finished. Comparing a time $s_1$ required until a gauge pressure within the casting chamber at a time of charging the gas at a pressure of 10 kgf/cm$^2$ (in the present specification, the internal pressure of the casting chamber is indicated by the pressure difference from the atmospheric pressure, the atmospheric pressure (1 atmospheric pressure) is 0, and a pressure equal to or less than 1 atmospheric pressure is indicated by a negative pressure) becomes 3 kgf/cm$^2$ with a time $S_2$ required until the gauge pressure within the casting chamber at a time of charging the gas at a pressure of 4 kgf/cm$^2$ becomes 3 kgf/cm$^2$, $S_1$ is smaller than $s_2$, and a rate of pressure increase $\theta_1$ at a time of charging the gas at the pressure of 10 kgf/cm$^2$ is larger than a rate of pressure increase $\theta_2$ at a time of charging the gas at the pressure of 4 kgf/cm$^2$.

Substituting this with the apparatus for casting the metal, when it is assumed that the pressure required for pressing the molten metal into the casting cavity 9 is 4 kgf/cm2, the set pressure value of the pressure adjusting device 11 is expected to be 4 kgf/cm$^2$, however, since the molten metal solidifies together with a passage of time, a lack of casting is generated if the casting is not executed within the time for which the fluidization can be executed. In particular, the metal having a high melting point such as the titanium or the like has a very short time that the fluidization can be executed, and there is generated a case that a complete casting formation can not be executed at the rate of pressure increase $\theta_2$.

FIG. 6 shows a relation between the gas supply pressure $P_1$ of the pressurized gas supply source 13 and the gas pressure $P_2$ required for casting the metal in the melting state within the casting cavity 9 of the casting mold 3 with no lack of casting, in the apparatus for casting the metal in accordance with the present invention.

As shown in FIG. 6, in accordance with the apparatus of the present invention, the gas supply pressure $P_1$ of the pressurized gas supply source 13 is greater than the gas pressure $P_2$ required for casting, and the time $s_i$ required until the internal pressure of the casting chamber gets to $P_2$ at a time when the gas supply pressure is $P_1$ is smaller than a time $s_0$ for which the molten metal can flow. In the case of executing the casting operation by using the apparatus in accordance with the present invention, a normal value of $P_2$ is between 1 and 3 $kgf/cm^2$, and a normal value of $P_1$ which satisfies a condition $s_1 < s_0$ is between 5 and 9 $kgf/cm^2$. In this case, a normal upper limit value of $P_1$ is 9 $kgf/cm^2$ because a withstand pressure of a normal casting chamber is set to be equal to 10 $kgf/cm^2$, and in the case that the casting chamber 1 has a withstand pressure structure capable of withstanding a further larger pressure, $P_1$ may be over 9 $kgf/cm^2$.

In accordance with the method of the present invention for casting the metal by using the apparatus mentioned above, after mounting the metal 4 on the crucible 2, the electric voltage is applied between the metal 4 and the electrode rod 10 so as to generate an arc discharge, and at a time when the metal 4 is melted so as to become in a state capable of flowing, the metal 4 in the molten state is poured into the casing port 5 of the casting mold 3 by tilting the crucible 2. Even during a period that the metal 4 in the molten state flows on the crucible 2 and drops down, the arc discharge current is controlled so that the arc discharge is kept between the metal 4 in the molten state and the front end of the electrode rod 10 (refer to FIG. 3(*a*)). Further, in accordance with the method of the present invention in which the metal casting is executed by using the pressurized gas, the control is executed so that the pressurized gas flows into the casing chamber 1 from the pressurized gas supply source 13 by setting the opening and closing valve 14 of the apparatus mentioned above in the open state at a time when the metal 4 molten on the crucible 2 is poured to the casting port 5 of the casing mold 3 due to the incline of the crucible 2, thereby shutting off the inflow of the pressurized gas within the casting chamber 1 by the opening and closing valve 14 at a time when the internal pressure of the casting chamber 1 gets to the gas pressure $P_2$ (refer to FIG. 3(*b*)).

EXAMPLE

Next, a description will be given of an experimental result at a time of executing an effective casting metal amount comparing experiment by using the apparatus for casting the metal in accordance with the present invention having the structure shown in FIG. 1, in a case (a) that the arc discharge is kept even during the period that the molten metal flows and drops down after the crucible starts tilting, and a case (b) that the arc discharge is stopped at the same time when the crucible starts tilting.

The effective casting metal amount (an effective rate) in the cases (a) and (b) mentioned above is obtained by executing the casting operation by using the casting mold 3 having the casting cavity 9 which is sufficiently larger than the volume of the metal 4 (an ingot before being molten), and measuring the metal weight charging the casting cavity 9 and a sprue (a value indicated by percentage by dividing this by the weight of the metal 4), in accordance with a lost wax method.

In each of the cases, a sample for estimation is obtained by executing six experiments in each of two kinds of metals 4 (size and weight).

| Used metal: | JIS second class titanium |
|---|---|
| Metal size (weight): | φ 30 mm × height 12 mm (40 g) |
| | φ 25 mm × height 12 mm (25 g) |
| Material of casting mold: | Celebest D |
| Sprue: | φ 3.2 mm × length 10 mm |
| Pattern: | φ 30 mm × height 15 mm |
| Temperature of casting mold: | 700° C. |

Pressurizing condition: pressure $P_1$ of the pressurized gas supplied within the casting chamber in a pressure reduction state (−70 cmHg, pressure 70 cmHg lower than a normal pressure) from the pressurized gas supply source 12 and gauge pressure $P_2$ within the casting chamber are as follows.

$P_1$=4 $kgf/cm^2$, $P_2$=3 $kgf/cm^2$

The effective casting metal amounts (effective rates) of the casting product obtained by the casting experiment mentioned above are shown in the following Table 1.

TABLE 1

| | | Effective rate in case that arc discharge is kept even after tilting of crucible is started numerals in parentheses denote effective casting metal amount | Effective rate in case that arc discharge is stopped at the same time when tilting of crucible is started numerals in parentheses denote effective casting metal amount |
|---|---|---|---|
| Weight of metal 4 | 40 g | 71.3% (28.5 g) | 53.8% (21.5 g) |
| | | 70.8% (28.3 g) | 55.5% (22.2 g) |
| | | 70.0% (28.0 g) | 54.3% (21.7 g) |
| | | 70.5% (28.2 g) | 52.0% (20.8 g) |
| | | 70.8% (28.3 g) | 55.3% (22.1 g) |
| | | 72.3% (28.9 g) | 54.5% (21.8 g) |
| | Average value | 71.0% (28.4 g) | 54.2% (21.7 g) |
| | 25 g | 81.6% (20.4 g) | 69.6% (17.4 g) |
| | | 81.2% (20.3 g) | 68.0% (17.0 g) |
| | | 81.2% (20.3 g) | 66.4% (16.6 g) |
| | | 80.8% (20.2 g) | 61.2% (15.3 g) |
| | | 81.2% (20.3 g) | 68.8% (17.2 g) |
| | | 80.4% (20.1 g) | 68.4% (17.1 g) |
| | Average value | 81.1% (20.3 g) | 67.1% (16.8 g) |

As shown in the experimental results in Table 1 mentioned above, even in the case of using the apparatus for casting the metal in accordance with the present invention, since the effective casting metal amount is larger and the metal amount leaving within the crucible after casting is smaller in the case that the arc discharge is kept even during the period that the molten metal flows and drops down after the crucible starts tilting in comparison with the arc discharge is stopped at the same time of the tilting operation of the crucible (corresponding to the case of using the conventional tilting type apparatus for casting the metal), it is possible to execute a very effective casting by using a minimum amount of metal.

INDUSTRIAL APPLICABILITY

In accordance with the apparatus for casting the metal of the present invention, since the arc discharge can be executed even during the period that the crucible tilts, it is possible to keep the melting state of the metal and the alloy which have the high melting point at a time of being casted within the casting mold, and it is possible to pour the molten metal to the fixed position, it is possible to obtain the casting product having a good quality, and it is suitable for casting the metal having the high melting point such as the titanium or the like which corresponds to the material particularly excellent as the prosthetic appliance for dentistry. Further, by employing the method in accordance with the present invention, the metal in the melting state can be casted within the time capable of flowing.

What is claimed is:

1. An apparatus for casting a metal which is suitable for casting a metal having a high melting point comprising:

a crucible (2) and a casting mold (3) provided in an interior portion of a casting chamber (1) capable of controlling an internal pressure;

an electrode rod (10) for melting a metal (4) mounted on said crucible (2) in accordance with an arc discharge, said electrode rod (10) being provided above said crucible (2);

said crucible (2) being tiltable around a supporting shaft (6) in such a manner as to pour the metal (4) melted on the crucible (2) into a casting port (5) of said casting mold (3);

said supporting shaft (6) being positioned in a side of an outflow end portion of said crucible (2) close to said casting port (5) ; and a tilting means (7) for drawing up a non-outflow end portion to an upper side so as to tilt the crucible, said tilting means (7) being provided in a side of the non-outflow end portion of said crucible (2), wherein said supporting shaft (6) is provided at a position at which a clearance between said metal (4) and a front end of said electrode rod (10) is kept substantially constant after the melting of the metal (4) in accordance with the arc discharge on said crucible (2) is started and the melting of said metal (4) makes progress and until the metal (4) in the melting state fluidizes and drops down due to the tilting of said crucible (2), and the arc discharge is controlled so that the arc discharge is carried over between the metal (4) in the melting state and the front end of said electrode rod (10) during a period that said crucible (2) is tilted and the metal (4) in the melting state fluidizes and drops down on said crucible (2).

2. An apparatus for casting a metal as defined in claim 1, wherein a pressure reduction pump (12) capable of making the interior portion of said casting chamber (1) in a pressure reduced state, and a pressurized gas supply source (13) supplying a pressurized gas to the interior portion of said casting chamber (1) are connected to said casting chamber (1), an inflow of the pressurized gas supplied from said pressurized gas supply source (13) into said casting chamber (1) is controlled by an opening and closing valve (14), said opening and closing valve (14).becomes in an open state at a time when a gas supply pressure $P_1$ of said pressurized gas supply source (13) is larger than a gas pressure $P_2$ required for casting the metal in the melting state into a casting mold cavity (9) of said casting mold (3) with no lack of casting and the metal (4) melted on said crucible (2) is poured into the casting port (5) of said casting mold (3) in accordance with the tilting of said crucible (2), and the inflow of the pressurized gas into said casting chamber (1) is shut off by said opening and closing valve (14) at a timing when the pressurized gas flows into said casting chamber (1) from said pressurized gas supply source (13) and an internal pressure of said casting chamber (1) gets to said gas pressure $P_2$.

3. A metal casting method of casting a metal comprising the steps of casting a metal having a structure in which a crucible (2) and a casting mold (3) are provided in an interior portion of a casting chamber (1) capable of controlling an internal pressure, providing an electrode rod (10) for melting a metal (4) mounted on said crucible (2) in accordance with an arc discharge is provided above said crucible (2), said crucible (2) is tiltable around a supporting shaft (6) in such a manner as to pour the metal (4) melted on the crucible (2) into a casting port (5) of said casting mold (3), said supporting shaft (6) is positioned in a side of an outflow end portion of said crucible (2) close to said casting port (5), and is provided at a position at which a clearance between said metal (4) and a front end of said electrode rod (10) is kept substantially constant after the melting of the metal (4) in accordance with the arc discharge on said crucible (2) is started and the melting of said metal (4) makes progress and until the metal (4) in the melting state fluidizes and drops down due to the tilting of said crucible (2), and providing a tilting means (7) for drawing up a non-outflow end portion to an upper side so as to tilt the crucible is provided in a side of the non-outflow end portion of said crucible (2), wherein an electric voltage is applied between said metal (4) and said electrode rod (10) so as to generate an arc discharge after mounting the metal (4) on said crucible (2), said crucible (2) is tilted at a timing that said metal (4) is melted so as to become in a state of capable of fluidizing, and the arc discharge is kept between the metal (4) in the melting state and the front end of said electrode rod (10) even during a period that the metal (4) in the melting state fluidizes on said crucible (2) so as to drop down at a time of pouring the metal (4) in the melting state into the casting port (5) of said casting mold (3).

4. A method as defined in claim 3, wherein providing a structure in which a pressure reduction pump (12) capable of making the interior portion of said casting chamber (1) in a pressure reduced state, and a pressurized gas supply source (13) supplying a pressurized gas to the interior portion of said casting chamber (1) are connected to said casting chamber (1), and an inflow of the pressurized gas supplied from said pressurized gas supply source (13) into said casting chamber (1) is controlled by an opening and closing valve (14) is used as said apparatus for casting the metal, and in which a gas supply pressure $P_1$ of said pressurized gas supply source (13) is made larger than a gas pressure $P_2$ required for casting the metal in the melting state into a casting mold cavity (9) of said casting mold (3) with no lack of casting, said opening and closing valve (14) is controlled so as to be in an open state at a time when the metal (4) melted on said crucible (2) due to the tilting of said crucible (2) is poured into the casting port (5) of said casting mold (3), and so that the pressurized gas flows into said casting chamber (1) from said pressurized gas supply source (13), and the inflow of the pressurized gas into said casting chamber (1) is shut off by said opening and closing valve (14) at a timing when an internal pressure of said casting chamber (1) gets to said gas pressure $P_2$.

* * * * *